(12) United States Patent
Ganz et al.

(10) Patent No.: US 7,796,254 B2
(45) Date of Patent: Sep. 14, 2010

(54) METHOD AND APPARATUS FOR DETERMINING PARTICLE SIZE AND COMPOSITION OF MIXTURES

(75) Inventors: Alan M. Ganz, Scarsdale, NY (US); Henry C. Weber, Scarsdale, NY (US)

(73) Assignee: August Ninth Analyses, Inc., Scarsdale, NY (US)

( * ) Notice: Subject to any disclaimer, the term of this patent is extended or adjusted under 35 U.S.C. 154(b) by 0 days.

(21) Appl. No.: 12/037,070

(22) Filed: Feb. 25, 2008

(65) Prior Publication Data

US 2008/0147339 A1 Jun. 19, 2008

Related U.S. Application Data

(62) Division of application No. 10/787,072, filed on Feb. 24, 2004, now Pat. No. 7,336,358.

(60) Provisional application No. 60/449,418, filed on Feb. 24, 2003.

(51) Int. Cl.
G01N 15/02 (2006.01)
G01N 21/00 (2006.01)
(52) U.S. Cl. ................................ 356/337; 356/335
(58) Field of Classification Search ......... 356/300–334, 356/402–425, 450–458
See application file for complete search history.

(56) References Cited

U.S. PATENT DOCUMENTS

| | | | | |
|---|---|---|---|---|
| 3,640,627 A | | 2/1972 | Beattie et al. | |
| 4,223,680 A | * | 9/1980 | Jobsis | 600/324 |
| 4,624,367 A | * | 11/1986 | Shafer et al. | 209/577 |
| 4,659,218 A | | 4/1987 | de Lasa et al. | 356/133 |
| 4,781,460 A | * | 11/1988 | Bott | 356/336 |
| 4,969,741 A | | 11/1990 | Kennedy et al. | 356/338 |
| 5,057,695 A | | 10/1991 | Hirao et al. | 250/575 |
| 5,155,549 A | | 10/1992 | Dhadwal | 356/336 |
| 5,676,142 A | * | 10/1997 | Miwa et al. | 600/310 |
| 5,740,291 A | * | 4/1998 | De Lasa et al. | 385/31 |
| 5,825,488 A | | 10/1998 | Kohl et al. | 356/342 |
| 5,874,726 A | * | 2/1999 | Haydon | 250/201.1 |

(Continued)

OTHER PUBLICATIONS

G. Kumar et al., Optimal probe geometry for near-infrared spectroscopy of biological tissue, Applied Optics, vol. 36, No. 10, pp. 2286-2293, Apr. 1, 1997.

(Continued)

*Primary Examiner*—Gregory J Toatley, Jr.
*Assistant Examiner*—Jarreas C Underwood
(74) *Attorney, Agent, or Firm*—David Aker

(57) ABSTRACT

A method for determining characteristics of a material includes illuminating the material with coherent light so as to produce scattered light; autocorrelating the scattered light; preprocessing a signal representative of the scattered light to produce a processed signal; and associating the analyzed data with particular characteristics of the material. At least one of a cumulant analysis and a cluster analysis may be performed to provide analyzed data. The determined characteristics may be used for real time control or termination a process used to alter the characteristics of the material. Specifically, monitoring of a process for changes in particle size as a function of time or to determine various physical and/or chemical characteristics of the particles or a mixture containing same, including homogeneity, may be achieved. An apparatus operating generally in accordance with the method is also disclosed.

22 Claims, 11 Drawing Sheets

U.S. PATENT DOCUMENTS

| | | | | |
|---|---|---|---|---|
| 5,905,271 | A * | 5/1999 | Wynn | 250/573 |
| 6,049,082 | A | 4/2000 | Methfessel | |
| 6,263,725 | B1 | 7/2001 | Garver et al. | 73/61.71 |
| 6,332,683 | B1 * | 12/2001 | Ono et al. | 351/210 |
| 6,474,354 | B2 | 11/2002 | Garver et al. | 137/2 |
| 6,519,032 | B1 * | 2/2003 | Kuebler et al. | 356/337 |
| 6,600,559 | B2 | 7/2003 | Switalski et al. | 356/336 |
| 6,615,061 | B1 | 9/2003 | Khalil et al. | 600/310 |
| 6,630,673 | B2 | 10/2003 | Khalil et al. | 250/341.8 |
| 6,635,224 | B1 * | 10/2003 | Gui et al. | 422/62 |
| 6,660,995 | B1 | 12/2003 | Canpolat et al. | 250/227.23 |
| 6,697,510 | B2 | 2/2004 | Moshe | 382/133 |
| 6,707,556 | B2 | 3/2004 | Turner et al. | 356/436 |
| 6,738,144 | B1 * | 5/2004 | Dogariu | 356/479 |
| 6,819,420 | B2 | 11/2004 | Kuebler et al. | 356/337 |
| 6,831,741 | B1 * | 12/2004 | De Kruif et al. | 356/338 |
| 6,917,424 | B2 * | 7/2005 | Rodrigues et al. | 356/326 |
| 2002/0135752 | A1 | 9/2002 | Sokolov et al. | 356/39 |
| 2002/0180972 | A1 * | 12/2002 | Ansari et al. | 356/336 |
| 2005/0018188 | A1 | 1/2005 | Arrivo et al. | |

OTHER PUBLICATIONS

J. M. Schmitt et al., Optical scattering properties of soft tissue: a discrete particle model, Applied Optics, vol. 37, No. 13, pp. 2788-2797, May 1, 1998.

J. P. Higgins et al., Spectoscopic Approach for On-Line Monitoring of Particle Size during the Processing of Pharmaceutical Nanoparticles, Analytical Chemistry, vol. 75, No. 8, Apr. 15, 2003.

* cited by examiner

METHOD AND APPARATUS FOR DETERMINING PARTICLE SIZE AND COMPOSITION OF MIXTURES

This application is a divisional of application Ser. No. 10/787,072 (now U.S. Pat. No. 7,336,358), which was filed on Feb. 24, 2004, which claims priority under 35 U.S.C. §119(e) from provisional patent application Ser. No. 60/449,418, filed on Feb. 24, 2003, the entire content of which is incorporated herein by reference.

BACKGROUND OF THE INVENTION

1. Field of the Invention

The present invention relates to the quantitative determination of analytical properties of chemical systems. More particularly to a method and apparatus for using broadband, preferably near-infrared light to determine both composition and particle size of colloidal mixtures. The present invention also relates to a method and apparatus for using narrow-band or laser light with autocorrelation techniques for characterizing variations in the properties of creams and lotions.

2. Prior Art

The classical method for obtaining absorbance spectra is via direct light transmission through a transparent sample. A polychromatic beam suffers a loss of intensity at particular wavelengths as it traverses a distance L, known as the path length, through a sample. Absorption of light is a consequence of interaction with the molecules of the sample, particular species favoring specific wavelengths of light. By calculating the ratio of the transmitted beam to the initial incident beam, one obtains the transmission spectrum. Taking the negative $\log_{10}$ of the transmission spectrum provides the more well-known absorption spectrum. In general, these systems are well described by Beer's Law, which shows that the absorbance is proportional to the path length.

Diffuse reflectance spectroscopy is the extension of this method to non-dilute, turbid, and even opaque samples. For these types of samples, light is backscattered, i.e., directed back in the same direction as it entered. Some of the light may have been absorbed as it penetrated the sample, analogous to phenomenon in transmission. In these systems, however, the path length is determined by the amount of scattering the light has undergone. The usual theory governing such systems is that of Kubelka-Munk.

Recent work applying diffuse reflectance to physiological systems has made use of modified measurement techniques while expanding the utility of these measurements. For example, the work of Schmitt and Kumar, "Spectral Distortions in Near-Infrared Spectroscopy of Turbid Materials" *Applied Spectroscopy*, 50, 8, pp. 1066-1073 (1996), which is hereby incorporated by reference in its entirety, was based on a variable separation distance between the optical fiber that introduced light into the system and the one that collected it. The authors show that by departing from the traditional back-scattering geometry of routine diffuse reflectance, they can detect variations of the absorption spectrum that might not have been expected. For example, they show that for a fiber separation of 6 mm, they could get an absorbance equivalent to a path length of 24 mm. They attribute this discrepancy to photon diffusion and demonstrate how to calculate the amount of absorption in such mixtures.

The critical feature that Schmitt and Kumar demonstrate is the dependence of the photon diffusion, and therefore the distortion of the spectrum away from the diffuse reflectance result, on the size of the particles doing the scattering.

Dynamic light scattering for particle size determination is usually done in dilute systems. Instead of a broadband source, laser light is used. The signal is autocorrelated to provide a measure of the fluctuation of the intensity as a function of time, usually on a microsecond—second time-scale. Particles undergo Brownian motion and the resulting dynamics impacts the intensity of the Rayleigh scattered light, generally causing a decreasing autocorrelation function which frequently appear to resemble exponential decay. When this signal is analyzed, diffusion coefficients, and inferentially, particle diameters can be deduced.

SUMMARY OF THE INVENTION

It is an object of the invention to provide a method and apparatus for monitoring particle size in a process wherein particle size of a material varies as a function of time.

It is a further object of the invention to provide a method and apparatus that characterizes particle size by reflection of light from the particles.

It is a further object of the invention to provide a method and apparatus that characterizes particle size by varying more than one parameter in the apparatus The invention comprises a method of determining the state of a mixture comprising, in general, both scattering and absorbing constituents, which comprises injecting light into the sample with a fiber optic; collecting light from the sample with a second fiber optic; spacing the fiber optics at a variable distance from each other, the coupling of injection and collection fibers being called a probe, and analyzing the reflected light with a spectroscopic analyzer. The variability of the spacing may be controlled by a mechanical stage driven by an electric motor. In turn, this motor may be operated by the computer that controls the spectrometer. Alternatively, the invention can be implemented by using multiple collection fibers strategically spaced with respect to the injector; using a multiplexing device to select the specific collection fiber to observe; and analyzing the reflected light from the selected fiber with a spectroscopic analyzer.

Such spectroscopic analyzer may be, but is not limited to, an FTIR, photodiode array, AOTF or grating spectrometer. Further, analysis involves comparing the suite of collected spectra with a comparable suite collected from a sample in the desired state ("finished product"); additionally or alternatively, calculating the average particle size or the particle size distribution based on the mathematical inversion of the photon diffusion equations; additionally or alternatively, calculating the average particle size or the particle size distribution from a database such as one that can be provided by autocorrelation methods (also known as "dynamic light scattering") or other analogous methods (acoustics, etc.).

Highly concentrated, virtually opaque, systems such as creams and lotions do not meet the criteria for analysis by this method. The particles are moving too slowly since they are large and likely to be in a viscous matrix. The systems multiply scatter, further confusing the traditional interpretation of the scattering signal.

Suspending the need to quantify a "particle size" has merit for characterization of such dense materials, however. In many cases a technician simply wishes to classify a material according to a series of known and reliable properties. Among these would be viscosity, color, sheen, and other variables known to have impact on the performance properties of the material. When the shape of the correlation function changes with sample we have a new means of making measurements in a class of materials heretofore unexamined by optical means.

The invention is straightforward, noninvasive and economical.

The invention is directed to a method for evaluating one or more materials in accordance with size of particles therein, comprising evaluating a spectrum of light reflected from a first group of particles; evaluating a spectrum of light reflected from a second group of particle; comparing results of the evaluating of the first group with results of the evaluating of the second group; and providing an indication of a state of the material when the comparing produces a predetermined comparison result.

The method may be used for monitoring a process wherein size of particles is changing as a function of time, and wherein the evaluating of a spectrum of light from a first group of particles comprises evaluating a spectrum of light reflected from the particles at a first time; the evaluating of a spectrum of light from a second group of particles comprises evaluating a spectrum of light reflected from the particle at a second time; the comparing results comprises comparing results of the evaluating at the first time with results of the evaluating at a second time; further comprising providing an indication of a state of the process when the comparing produces predetermined comparison results. The evaluating may be done so that at least one of the first time and the second time occurs during the process. The evaluating at least one of the first time and the second time may be an evaluating of a reference sample at a time other than during the process.

The method may further comprise varying distance between a first light conductor for conducting light to the particles and a second light conductor for conducting light from the particles for the evaluations, and evaluating spectra of light received from the particles at a plurality of distances between the first light conductor and the second light conductor. The distance may be varied to eliminate spurious reflections from the groups of particles or from a container in which the particles are disposed.

The particles may be in a liquid, and selected from a group comprising at least one of solid particles and liquid droplets.

The method may further comprise moving, at a plurality of different times, a first light conductor for conducting light to the particles and a second light conductor for conducting light from the particles along a column containing the liquid. The method may further comprise determining at least one of a rate of motion of an interface in the liquid, and characteristics of particles in a vicinity of the interface. The method may further comprise determining characteristics of particles on opposite sides of the interface.

The method may also further comprising determining compositional characteristics of the particles by analyzing at least one of the spectra, the compositional characteristics including at least one of particle size and chemical composition.

The first group of particles and the second group of particles may be successive groups of particles in a batch of particles undergoing a process of mixing, and the evaluating of the particles may be performed at different times, to obtain an indication of homogeneity of a mixture containing the particles.

The first group of particles and the second group of particles may be successive groups of particles in a process flow stream.

The first group of particles and the second group of particles may be successive groups of particles in a process, and the method may further comprise using the results of the evaluating to monitor changes in characteristics of the particles to obtain an indication of homogeneity of the particles.

The method may be used to perform at least one of classification of materials, monitoring of a process, determining authenticity of a product, and determining quality of a product. The method may also be used to determine size of particle in at least one of the first group of particles and the second particles. The at least one group of particles may be suspended in a liquid characterized by a series of parameters and the size of the particles may be determined by utilizing a predetermined relationship between values of the parameters, a spectrum of reflected light from the particles and the particle sizes. The distance between a first light conductor for conducting light to the particles and a second light conductor for conducting light from the particles for the evaluations may be varied, and the utilizing repeated at a plurality of distances.

The invention is also directed to a method for determining characteristics of a material comprising illuminating the material with coherent light so as to produce scattered light; autocorrelating the scattered light; preprocessing a signal representative of the scattered light to produce a processed signal; performing at least one of a cumulant analysis and a cluster analysis to provide analyzed data; and associating the analyzed data with particular characteristics of the material.

The invention is also directed to an apparatus for evaluating one or more materials in accordance with size of particles therein, comprising means for evaluating a spectrum of light reflected from a first group of particles and from a second group of particles; means for comparing results of the evaluating of the first group with results of the evaluating of the second group; and means for providing an indication of a state of the material when the comparing produces a predetermined comparison result.

The apparatus may be used for monitoring a process wherein size of particles is changing as a function of time, and wherein the means for evaluating of a spectrum of light from a first group of particles comprises apparatus for evaluating a spectrum of light reflected from the particles at a first time and at a second time; the means for comparing results comprises comparing apparatus for comparing results of the evaluating at the first time with results of the evaluating at a second time; further comprising means for providing an indication of a state of the process when the comparing produces predetermined comparison results. The means for evaluating evaluates at the first time and at the second time, during the process.

The apparatus may further comprise a storage device for storing a reference produced at a time other than during the process, for evaluating at least one of the first time and the second time.

The apparatus may further comprise means for changing distance between a first light conductor for conducting light to the particles and a second light conductor for conducting light from the particles for the evaluations, and means for evaluating spectra of light received from the particles at a plurality of distances between the first light conductor and the second light conductor. The apparatus may further comprise means for containing a liquid in which the particles are dispersed and means for moving, at a plurality of different times, a first light conductor for conducting light to the particles and a second light conductor for conducting light from the particles along the means for containing the liquid.

The apparatus may further comprising means for determining a rate of motion of an interface in the emulsion, and means for determining characteristics of particles in a vicinity of the interface, as well as means for determining characteristics of particles on opposite sides of the interface or in a vicinity of the interface.

The apparatus also may further comprise a flow cell through which a mixture containing the particles flows in order to have measurements performed thereon. The flow cell may be positioned to evaluate raw materials entering a process or to evaluate materials during a process.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1A:
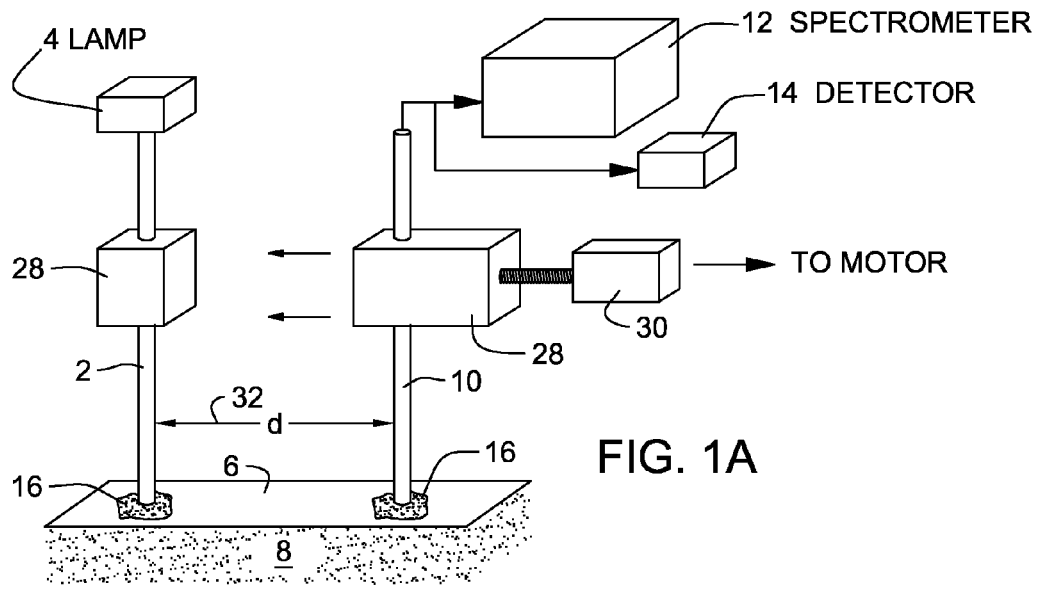
FIG. 1A is a perspective view of a first form of an optical probe in accordance with the invention.

Referring to FIG. 1A, there is shown a perspective view of an apparatus 10 incorporating features of the present invention. Although the present invention will be described with reference to the various embodiments shown in the drawings, it should be understood that the present invention can be embodied in many alternate forms of embodiments. In addition, any suitable size, shape or type of elements or materials could be used.

FIG. 1A shows the basic configuration of the system. A fiber optic or bundle 2 directs light from a source or lamp 4 onto a sample. There may be a transmission window or sight glass 6 that abuts the sample 8 to be studied. A second fiber optic or bundle 10 collects light from the sample and directs it to a spectrometer 12 and/or a detector 14. In an equivalent configuration, the light entering through bundle 2 may already have been predispersed. The spectrometer 12 may be a photodiode array instrument such as those made by Ocean Optics or Micron Optical Systems, an AOTF such as those made by Brimrose, or an FTIR such as those made by PerkinElmer.

To minimize reflections from the glass 6, the glass may be treated with antireflection coating at the wavelengths used in the system. Alternatively, there may be a drop of index matching fluid 16 between the fibers and the glass.

Figure 1B:
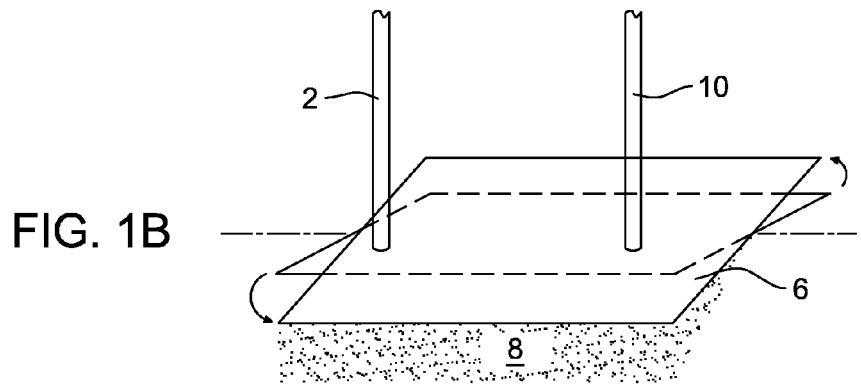
FIG. 1B illustrates a possible geometry of a view port and a probe for the optical probe of FIG. 1.

Another way to minimize back reflections is to rotate the angle at which light from the fibers meet the plane of the glass, as is shown in FIG. 1B.

Varying the separation of the fibers will also tend to reduce spurious reflections at various distances between the fibers.

Figure 1C:
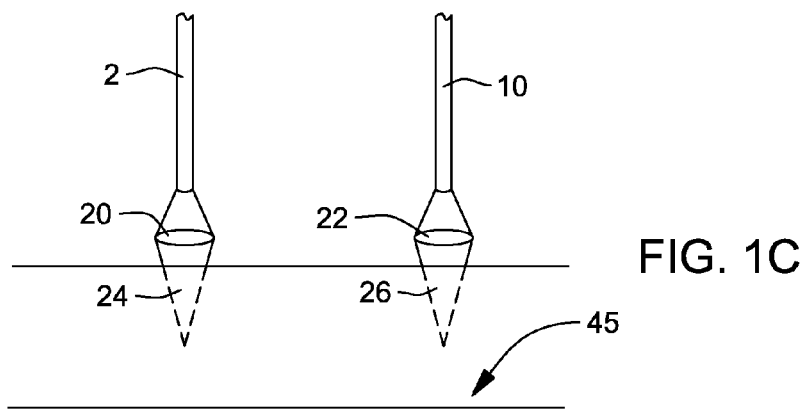
FIG. 1C illustrates focusing optics for the optical probe of FIG. 1

In yet another configuration, shown in FIG. 1C, one or more of the fibers may be positioned with a focusing lens 20 or a collecting lens 22 to allow imaging into portion 24 or from portion 26 of the sample. The sample may be in a flow cell 45. It is important to note that variation of the focus position and/or the collection position of the lenses is another degree of freedom with which to examine the system, analogous to d.

A support block 28 that holds the fibers is attached to a micropositioner 30, such as a single axis translation stage made by Newport Corporation, to move the fibers to the desired separation distance d 32. The translation stage may be driven by a motor which can be interfaced to a computer to provide an integrated method of collecting spectral data at variable inter-fiber spacings, d. When d is close to zero, the system is in the backscattering mode, the standard diffuse reflectance configuration.

Spectra $S_d$ are collected by sets $\Sigma$ with $\Sigma$ consisting of at least one, but generally a plurality of spectra, at specified d values. Such sets are called "movies" since, in general, they are snapshot spectra done in multiple positions or framers. For example, a set may consist of $S_0$, $S_2$, $S_5$, and $S_{10}$, where the subscripts denote the size of d in millimeters. Traditional diffuse reflectance measurements are a special case of $\Sigma$, containing only $S_0$.

Data may be used in single-beam mode. In a preferred form, data may either be normalized by an absolute intensity as in the method of Schmitt and Kumar, or the data of $\Sigma$ may be divided by $S_0$ to observe deviations in the relative amplitude of the peaks of the various spectra. Thus, when the effect of increasing d is merely to uniformly increase the path length across the available spectrum, the new ratios, $S_d/S_0$ will all be flat lines.

Since scattering depends on the ratio of the wavelength of the incident light $\lambda$ to the size R of the scattering particle (assumed spherical for simplicity), when $\lambda/R \gg 1$, the particle is an isotropic scatterer. For large particles, i.e., when $\lambda/R \approx 1$, the scattering tends to beam in the forward direction. Two phenomena are anticipated:

1. As $\lambda/R$ increases, more light is directed outward toward the large d values. This happens because the isotropically scattered beam has components going in every direction, including parallel to the interface. By contrast, large particles, which scatter in the forward direction, lack a significant component in the direction transverse to the direction of the injected light. Of course, it is the presence of multiple scattering that enables detection at significant d values in the first place.

2. Within a spectrum, there is a chromatic effect. For example, for a bandwidth of 800 nm with $\lambda$ going from 800 nm to 1600 nm there is a wide difference in $\lambda/R$ ratios. At the blue end, where $\lambda$ is smallest, particles appear to act larger than at the red end. These phenomenologies can be used to advantage in several ways:

Particle Size and Composition

A series of $\Sigma$ measurements may be made to represent the time evolution of a mixture as it is being mixed and or milled. In this process particles are frequently made smaller. Thus, the scattering properties of the mixture varies, or $\Sigma$ is really $\Sigma(t)$ where t is time. At some time $t_f$ the mixture will be completed. However, $t_f$ may vary due to a variety of external factors such as mixing/milling rate, initial size of particulates, etc.

If the $\Sigma(t_f)$ data is available, then a real time comparison of $\Sigma(t)$ can be done. To obtain $\Sigma(t_f)$ a sample of the product that is considered to be of acceptable quality as determined by whatever standards are normally employed is separately measured. The quality standards will differ from product to product. For a food it might be texture, viscosity, or some other variable or set of variables. For a cosmetic it may be sheen or transparency. Nevertheless, each of these acceptably finished products can be linked with a $\Sigma$ simply by measuring a sample. This $\Sigma$ is by definition the $\Sigma(t_f)$.

In general, it will be possible to store a time evolution of $\Sigma$ so that not only will it be possible to determine if a mixture is ready, but also how far along the process it is.

Figure 2:
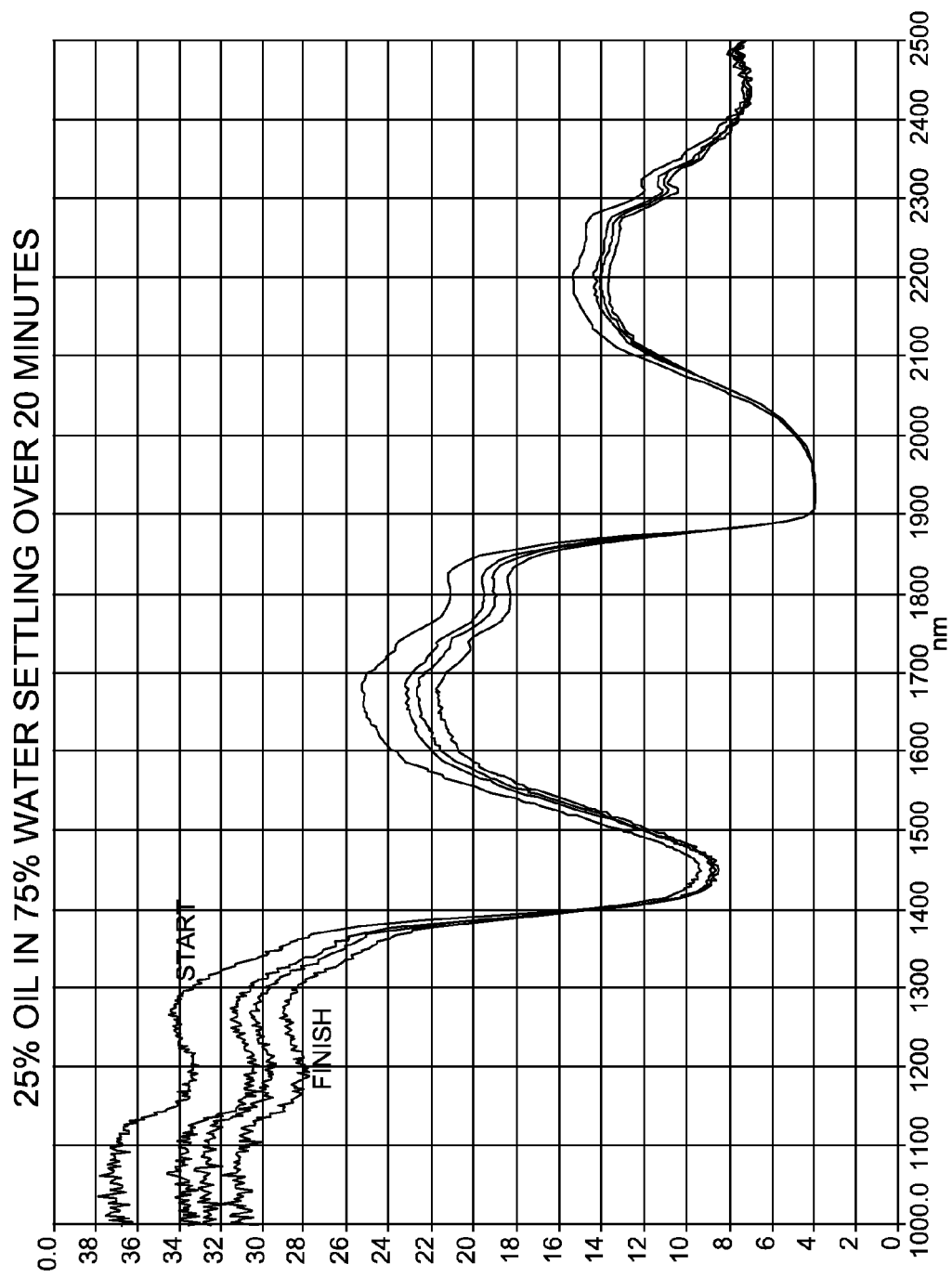
FIG. 2 illustrates the change of diffuse reflectance response as an emulsion system breaks.
Figure 3:
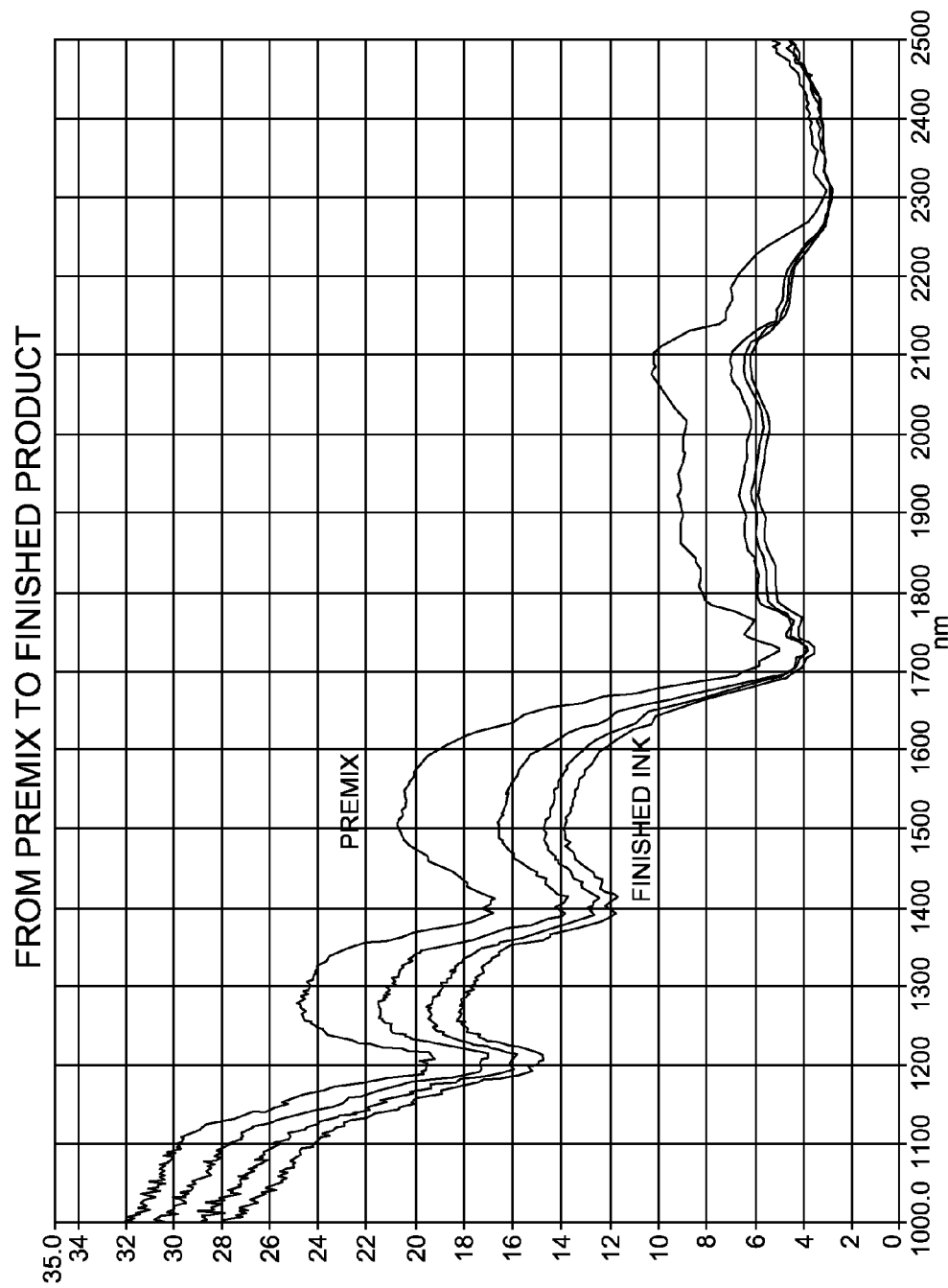
FIG. 3 illustrates the change of diffuse reflectance response as a solid-particle system is milled.

FIGS. 2 and 3, which are representations of a $\Sigma$ with only an $S_0$, i.e., a fixed spacing, backscattering probe, show that near IR radiation can be scattered back from particulate matter in liquid dispersions and that the resulting near IR spectrum provides information about both system composition and particle size. Additionally, the figures demonstrate that particles may be either self-forming droplets, as emulsions, or solid materials like minerals.

It is universally known, that when water and an oil, like canola oil, are shaken together the two liquids form an emulsion. Basically globules of oil in water or water in oil are formed. It is also well known, that the shaken system will eventually settle out and the oil phase will once again settle above the water phase. In the process, the moderate size emulsion droplets that had been created upon shaking, agglomerate. They then grow to larger droplets until the "droplet" size becomes the whole phase.

The spectrum of the emulsion system changes as the emulsion breaks, as seen in FIG. 2. These spectra were taken with an external Galileo probe using an indium antimonide detector. The Galileo probe is a fixed spacing, back-scattering fiber optic probe connected via the external port to a PerkinElmer FT spectrometer. Bright (100+) inkjet paper was used as a neutral reference background, so these reflectance spectra have units analogous to those for transmission spectra, i.e. percent reflected. The prominent water peaks around 1450 nm and 1900 nm are clearly seen in the emulsion reflectance spectra. So, too are the structures of canola oil at 1700-1800 nm as well as in the 1200 nm and 2300 nm regions. Thus, the system composition spectra can be recognized.

But additionally, as a function of time, the spectra move in a downward direction. In other words, as the particles get bigger, the spectrum shifts downward. The number of particles is also decreasing since virtually all the oil in this 25% oil emulsion system is used up to make droplets. As the droplet size increases, the additional oil comes at the expense of sacrificing other particles. In this case there is also a moderate shape change as evidenced by the difference in the spectra below 1350 nm and again between 1600 and 1900 nm.

Figure 4:
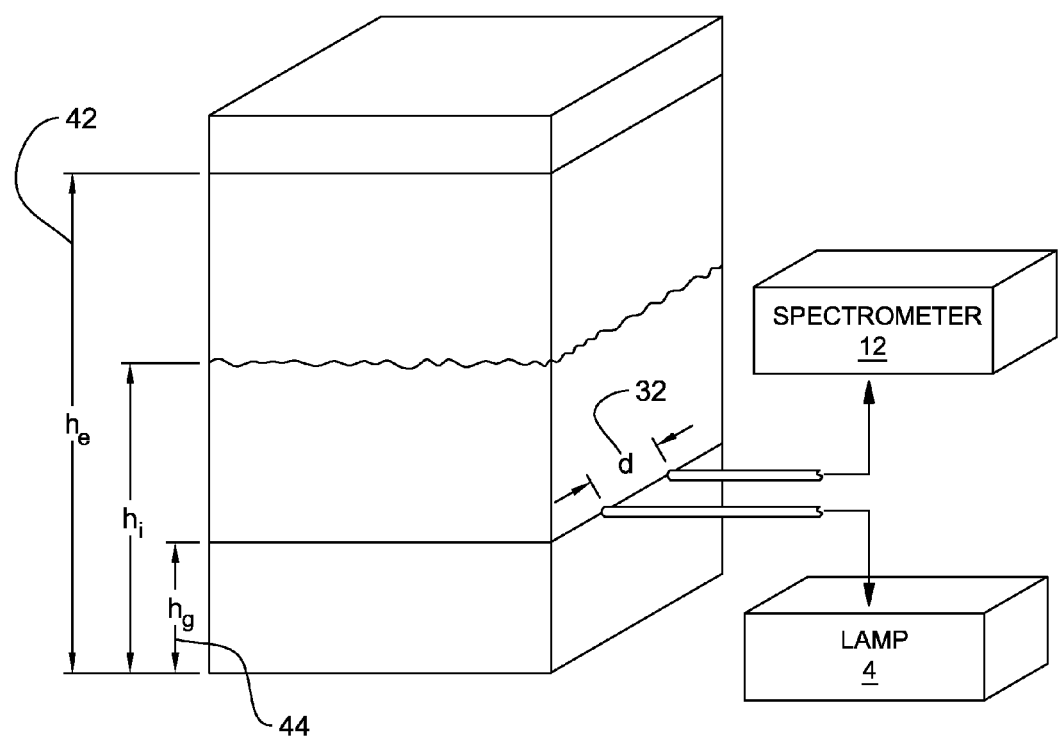
FIG. 4 illustrates an apparatus in accordance with the invention for measurement of emulsion stability.

Samples of ink in the process of being milled were obtained by removal from the process wet-millers at different stages of completion. FIG. 4 illustrates a downshift in the near IR spectrum in the course of this process.

The ink goes from starting as a premix at the very top spectrum, through 2 manufacturing passes and then down to a final product as the lowest spectrum.

Not all sample spectra move downward in time. Other data, not shown, exhibit a rise in spectral position as milling proceeds.

The conclusion is that the near-IR spectrum, can in addition to showing details of chemical composition by the position of spectral peaks, also shows the relative particle size of mixtures of particles dispersed in a fluid. These particles could be liquid themselves, as with emulsions, or they could be solid materials as with the inks and dyes.

Emulsion Stability Analysis

Emulsions are intrinsically unstable mixtures. It is frequently necessary to know the stability lifetimes for a variety of products. For example, the anticipated shelf life of creams and foods is in part determined by the phase stability of the product. Since the invention is a sensitive detector of both scattering (relating to particle size) and absorption (relating to chemical composition), it is useful in determining the status of an emulsion by moving the fiber optic probes to scan along the height $h_s$ 44 of a container with emulsion filled to height $h_e$ 42, as shown in FIG. 4. The light source or lamp 4, and the spectrometer, 12 are shown.

The apparatus can be moved vertically along the column of a separating emulsion 40. Initially, all $\Sigma$ will be virtually identical since the system is approximately uniform. As the system begins its phase separation, an interface will form, shown at height $h_i$ and $\Sigma$ will vary. For example, if the intial mixture were a simple oil and water emulsion, the $\Sigma$ data will evolve such that ultimately there will be a uniform set of them along the bottom section of the column, corresponding to the water phase, and a very different set of $\Sigma$ values in the upper part of the column for the oil phase. However, considerably before full separation, it will be apparent that there is a discontinuous change in the $\Sigma$ pattern. This discontinuity corresponds to the interface that is evolving.

In principle, only one measurement, taken at a constant spacing, d, which could be zero, may be needed. However, by taking multiple frames at differing inter-fiber separations, the analysis may be improved.

Average Particle Size and/or Particle Size Distribution

Another objective of the invention is to determine average particle size and/or particle size distribution. Inasmuch as both the magnitude of light at increasing d values (item 1 above) and the relative amount of modification (or distortion) of the backscattered spectrum $S_0$ as seen at higher d values (item 2 above) are a byproduct of particle size, there is data to be mined.

Another feature to consider is that scattering behaves as $\lambda^{-n}$ where n goes from approximately 4 in the Rayleigh (small particle) regime to <1 in the Mie (large particle) regime.

A way to process this data is to use samples of colloidal suspensions, preferably ones that can be diluted, and independently determine particle size. Next perform a multivariate analysis on $\Sigma$ to extract the information. An example is a suspension of paint pigment, which unlike emulsion droplets, can be diluted in a routine manner. The diluted sample can then be measured with correlation techniques (dynamic light scattering).

Polydispersity or average particle size can be forward modeled from the equations in Scmitt and Kumar's work simply by summing up the results from their calculations on monodisperse materials. Despite the fact that their calculation in equation 1 from the cited reference is the result of a random diffusion model, their results are dependent on entirely measurable quantities. Thus, in their modeling, they predict the reflectance of a system based on absorption coefficients, volume fractions of materials, surface reflectivities and, importantly, scattering cross sections. These cross sections are themselves based on mean volume of spheres. Thus, for a measured reflectance and with all other properties but size known, a trial-and-error fit can be made to match the observed spectrum to the various trial particle sizes.

Furthermore, the spectra calculated by Schmitt and Kumar are functions of the inter-fiber distances. By making a plurality of measurements at differing fiber spacings, a suite of spectra can be obtained. A best fit of the predicted spectra to the suite as a function of spacing using the estimated particle size would provide an optimal result.

This method could be extended to trial distributions of particles to fit a hypothesized particle size distribution to the measured reflectance. Ideally, this would be after selection of a size probability distribution and integrating over particle size. Thus, for example, if one assumed N different particle sizes, one could generate N diffusion equations and sum them up, suitably weighted, to give an overall prediction of spectral changes form polydisperse mixtures.

Figure 5:
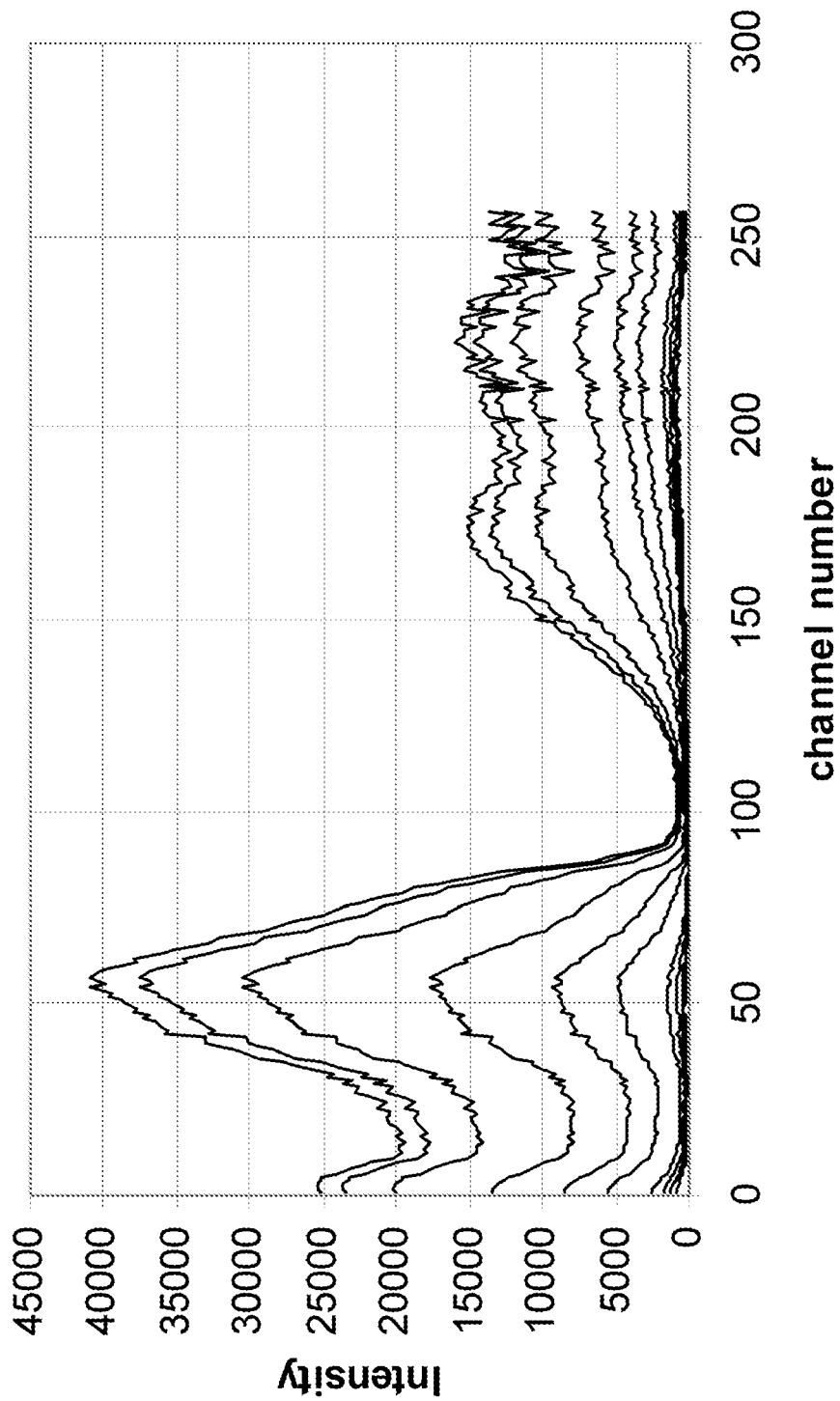
FIG. 5 shows spectra formed by separation of sender and receiver fibers.

Utilizing a probe with a variable distance between the fiber that injects light into the sample (the sender) and the fiber that collects the reflected light (the receiver), results in different positions providing variable overall intensities. FIG. 5 shows a suite of such spectra for a finished commercial cream.

Figure 6:
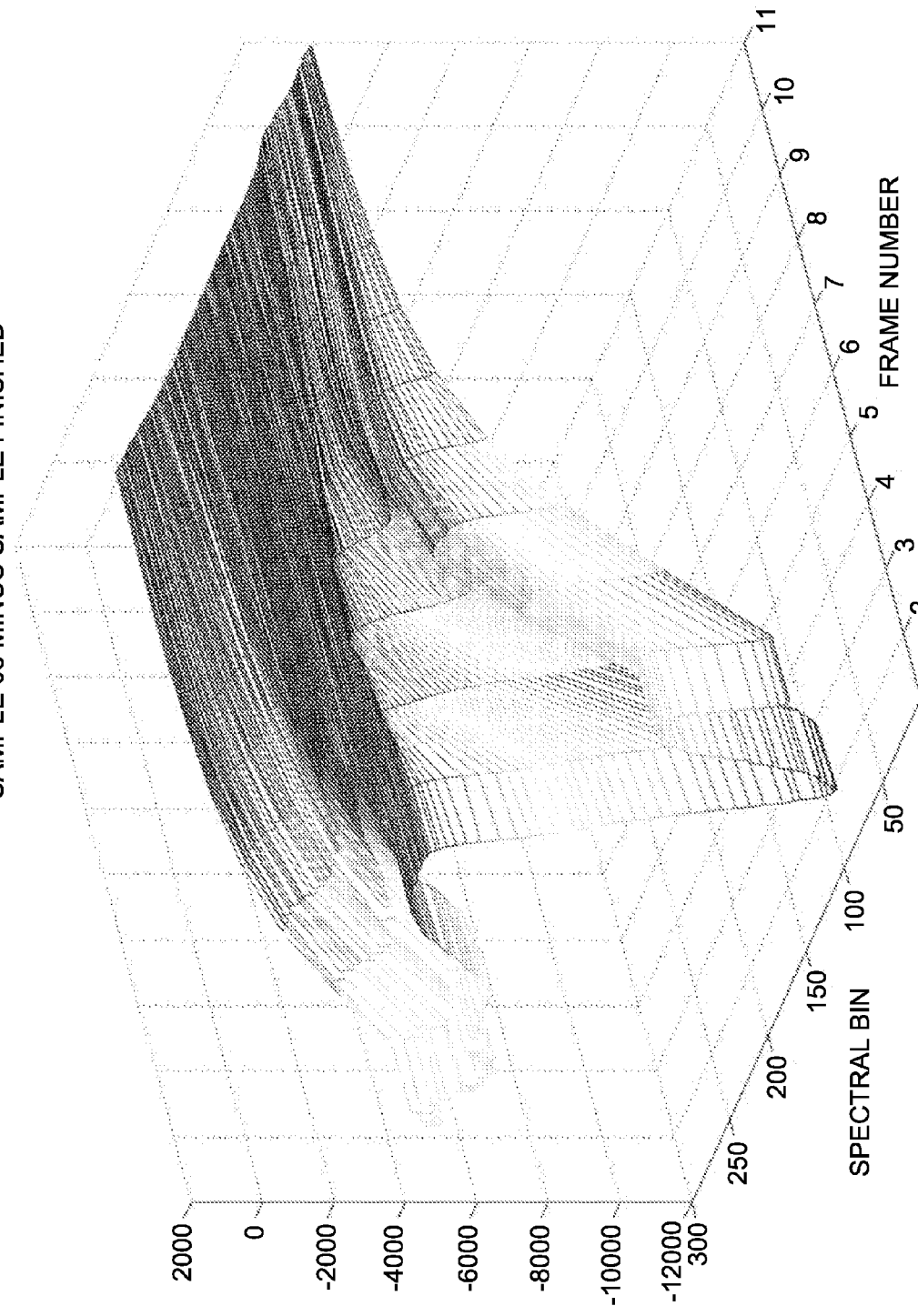
FIG. 6 is a full 11-frame movie of sample subtracted from that of finished product.

When a fixed probe is used, comparison between different samples can be achieved simply by overlaying their respective spectra and noting variations. The customary way to do this is to subtract one spectrum from the other. The closer the residuals are to zero, the more nearly alike are the two spectra, and therefore, the more nearly alike are the samples themselves. The analogous situation when comparing the suite of spectra, called the movie, is shown in FIG. 6. This, too, is a subtraction, but it generates a two-dimensional surface because the individual movie frames are plotted one behind the other in a 3-arrangement.

If the sample is finished product, its movie is the same as that of the movie of FIG. 6. The 3-D plot then collapses into a flat sheet at zero because all of the respective frames have matched spectra. In fact, the data at the higher frame numbers appears to be very close to zero, providing the impression that the two samples are well-matched at higher frame numbers. Such a conclusion would be misleading for the following reason: as FIG. 5 shows, the raw spectral data is much smaller at high frame numbers than at low ones. Consequently, subtracting two small numbers is bound to leave a small number as a remainder. For the early frames, where signals can exceed 30,000 counts, even a 3% variation is 900 counts, a value larger than some of the spectra in the later frames.

Figure 7:
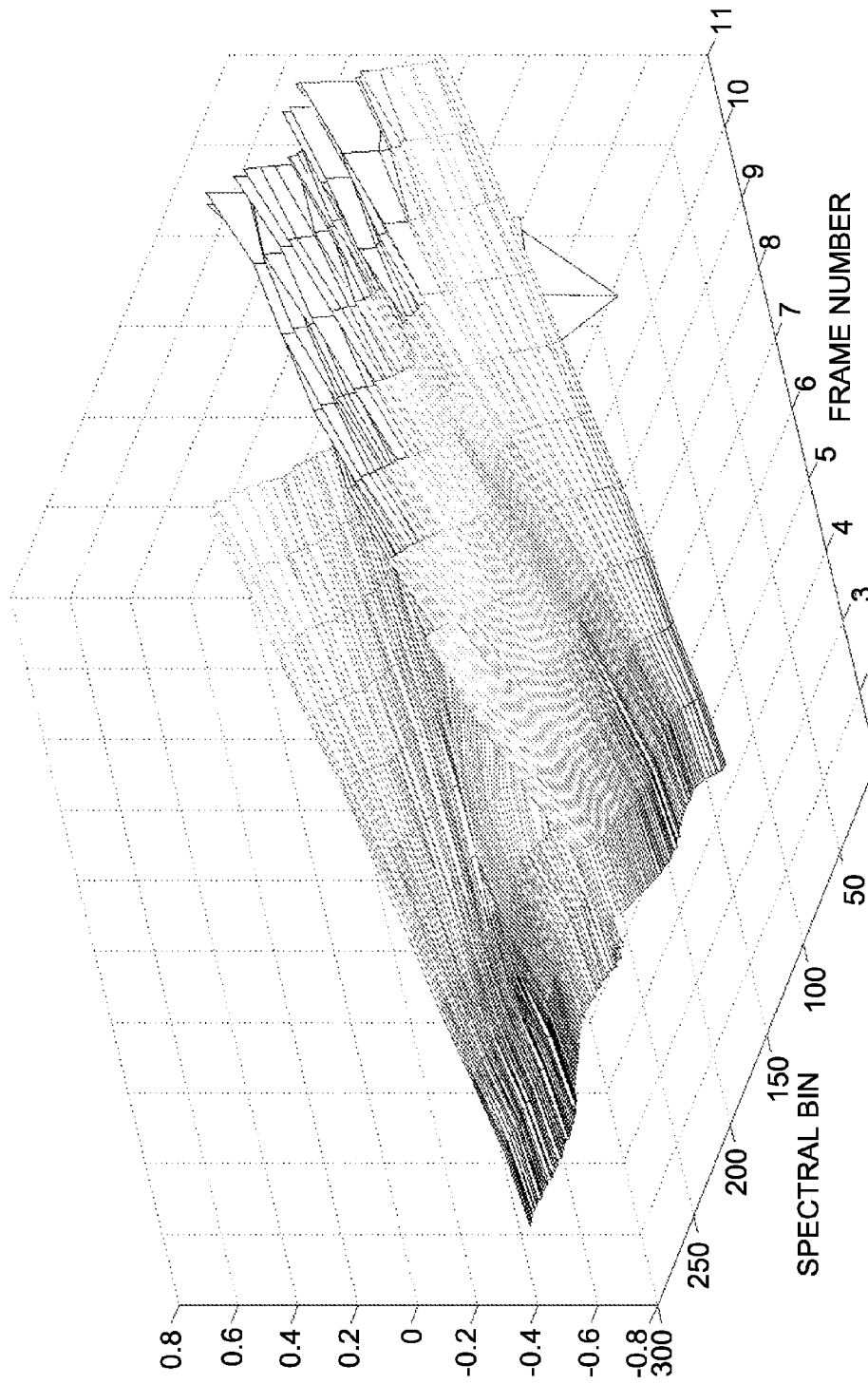
FIG. 7 is a fractional deviation movie.

To improve the balance of the subtraction, a weighted difference is taken in place of the raw difference. In one implementation the two spectra in a particular frame number are subtracted from each other, as before, but in addition the difference is divided by the spectrum of the finished product in a point-by-point manner. This scheme provides equal weighting to all the frames. Naturally, a more complex set of weights may be assigned if unequal weighting is appropriate. For example, a weighting that is proportional to the magnitude of the signal or to the square root of the signal might be chosen, where by "signal" the integrated area under the curve is meant. Other possibilities for defining signal could be considered. In effect, a fractional change in the spectrum is calculated. See FIG. 7.

Under these conditions, the smoothness in the high-frame-number region is now replaced with a bumpy (positive and negative deviations) structure. The process of normalizing the data to provide a fractional difference rather than an absolute difference is seen therefore to improve the ability to discern variations in the data that are real and independent of frame number.

This tool can be applied to a set of samples measured on the near IR instrument. The objective is to determine which samples appear to be most similar to other samples and, correspondingly, which are most different.

Since the objective is to find the degree of dissimilarity between samples, the best way to begin this effort is by taking multiple data sets on a single sample. Thus, three runs were performed on each particular sample, with the container moved to a fresh location between runs. Inasmuch as these data should be very close to each other, this triplet sets a minimum standard of variation that should be expected to be detectable.

The comparison was made by:
1. Taking the mean spectrum of all three runs for each frame.
2. Subtracting the mean spectrum from each of the three using the weighting previously described.
3. Tabulating the results according to frame number.

Table 1 shows reproducibility errors of 5 creams as a function of frame number. The table entries can be considered to be the overall percent error of mismatch between the specific run and the mean of the three runs. Thus, the errors are the difference between the mean of the three runs and the individual spectra. The larger deviation errors in the higher frames could be a useful indicator for unequal weighting of the subtraction data. For example, the weighting could be set to be inversely proportional to the deviation.

TABLE 1

| Sample | Frame #: 6 | 7 | 8 | 9 | 10 | 11 | Avg frame 10 |
|---|---|---|---|---|---|---|---|
| A | 0.8665 | 1.6043 | 2.2022 | 4.0425 | 4.9299 | 21.5796 | 4.93 |
|   | 0.9176 | 1.5954 | 1.8449 | 3.0223 | 5.1271 | 7.5346 |  |
|   | 1.4925 | 2.4445 | 2.7322 | 4.3738 | 4.7347 | 4.8567 |  |
| B | 0.9038 | 2.1543 | 3.5576 | 26.1307 | 86.4859 | 311.7983 | 181.07 |
|   | 0.8945 | 1.8154 | 18.7277 | 213.3659 | 254.6579 | 39.4301 |  |
|   | 0.4202 | 1.3836 | 10.6072 | 13.2979 | 202.0071 | 16.6333 |  |
| C | 0.5055 | 0.6771 | 2.0096 | 5.4930 | 5.3456 | 30.5588 | 6.81 |
|   | 0.4884 | 1.1762 | 1.5923 | 2.3089 | 4.3520 | 9.1865 |  |
|   | 0.4840 | 0.7941 | 1.7240 | 4.6256 | 10.7439 | 7.7015 |  |
| D | 0.2636 | 0.4805 | 0.8893 | 1.1330 | 1.8702 | 8.2100 | 2.75 |
|   | 0.2208 | 0.4094 | 0.9781 | 1.3273 | 3.0086 | 7.4759 |  |
|   | 0.2577 | 0.6256 | 1.0410 | 2.7476 | 3.3683 | 5.5424 |  |
| E | 0.3231 | 0.3922 | 0.6993 | 2.6934 | 3.2948 | 48.9279 | 2.17 |
|   | 0.2944 | 0.3910 | 0.5748 | 1.6568 | 1.5629 | 2.3534 |  |
|   | 0.2388 | 0.4768 | 0.6467 | 1.4660 | 1.6531 | 34.5727 |  |

Figure 8:
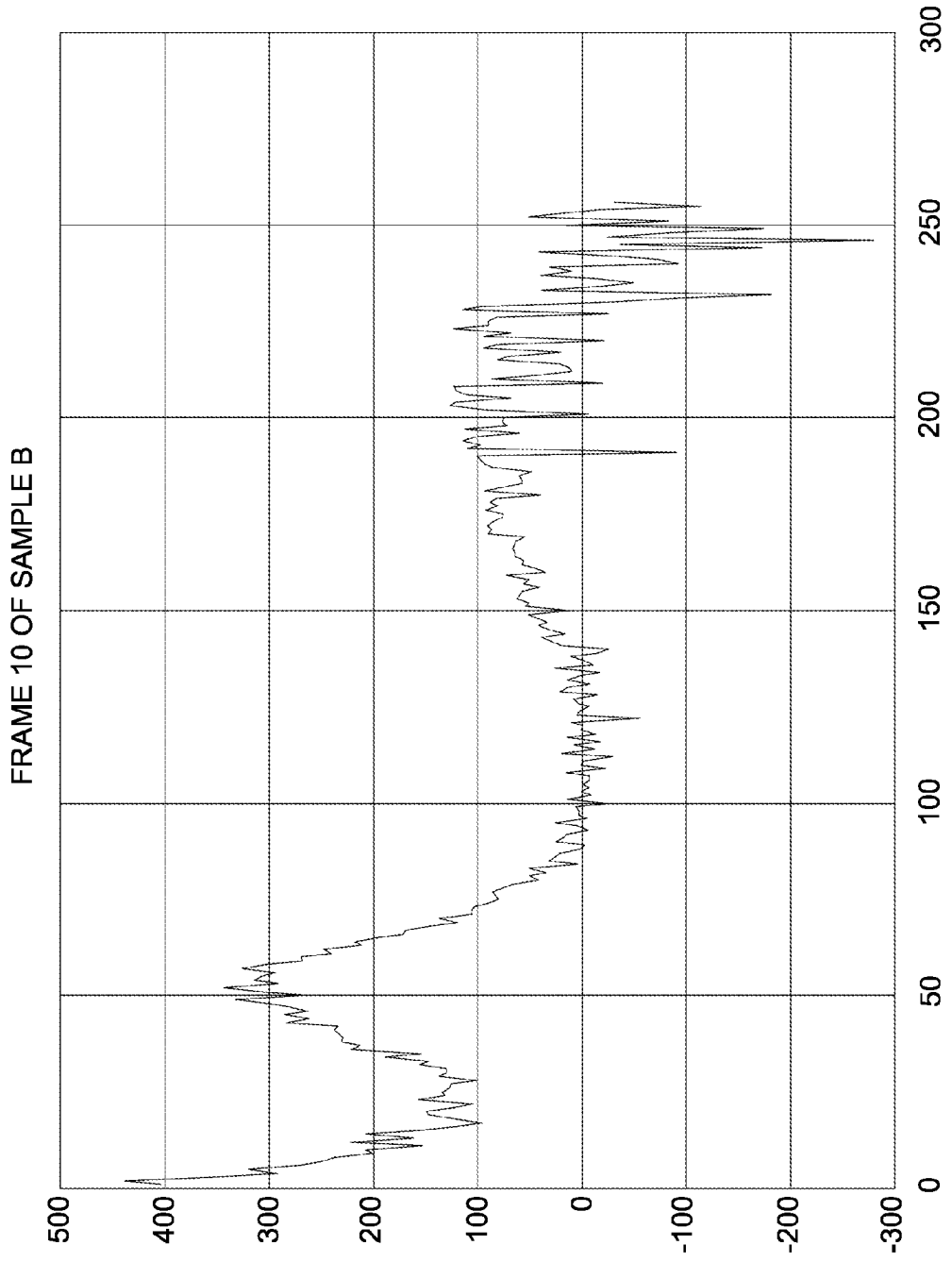
FIG. 8 is an example of a frame where noise pushes the signal negative.

If frame 10 is (arbitrarily) chosen as the benchmark, samples A, C, D and E appear to reproduce to about 7% or better, but sample B shows mismatches as high as 180%. This enormous error is fortuitous. The attempt to put all the frames on an equal footing by taking a ratio of the differences to one of the spectra has a built-in limitation at numbers near zero. Reference is made to FIG. 8 as an example.

An artifact is introduced in attempting to weight data points with very small numbers to the same degree as the larger amplitude points. To reduce the effect of this undesired situation, another technique is added: windowing. The region (window) from pixels 90 to 130 is cut out of the data analysis entirely. When this is done, the errors in all the points in table 1 go down in magnitude. The summary for frame 10 can be seen in Table 2.

TABLE 2

|   | Full spectrum | Windowed Spectrum |
|---|---|---|
| A | 4.93 | 4.26 |
| B | 181.07 | 84.54 |
| C | 6.81 | 1.89 |
| D | 2.75 | 1.14 |
| E | 2.17 | 0.48 |

Three out of the five examples provide excellent repeatability when the bottom-scraping data points are eliminated. A fourth one, A, provides respectable results. B, though much improved is clearly an example of poor data. This suggests that the integrity of a sample data set should be inspected prior to moving on to another sample.

A closer look at FIG. 8 shows that at high bin values, (approximately 240), there is another drop in the spectrum toward zero. A comparison between B and another sample is illustrative of what a good quality control measure can provide.

Figure 9:
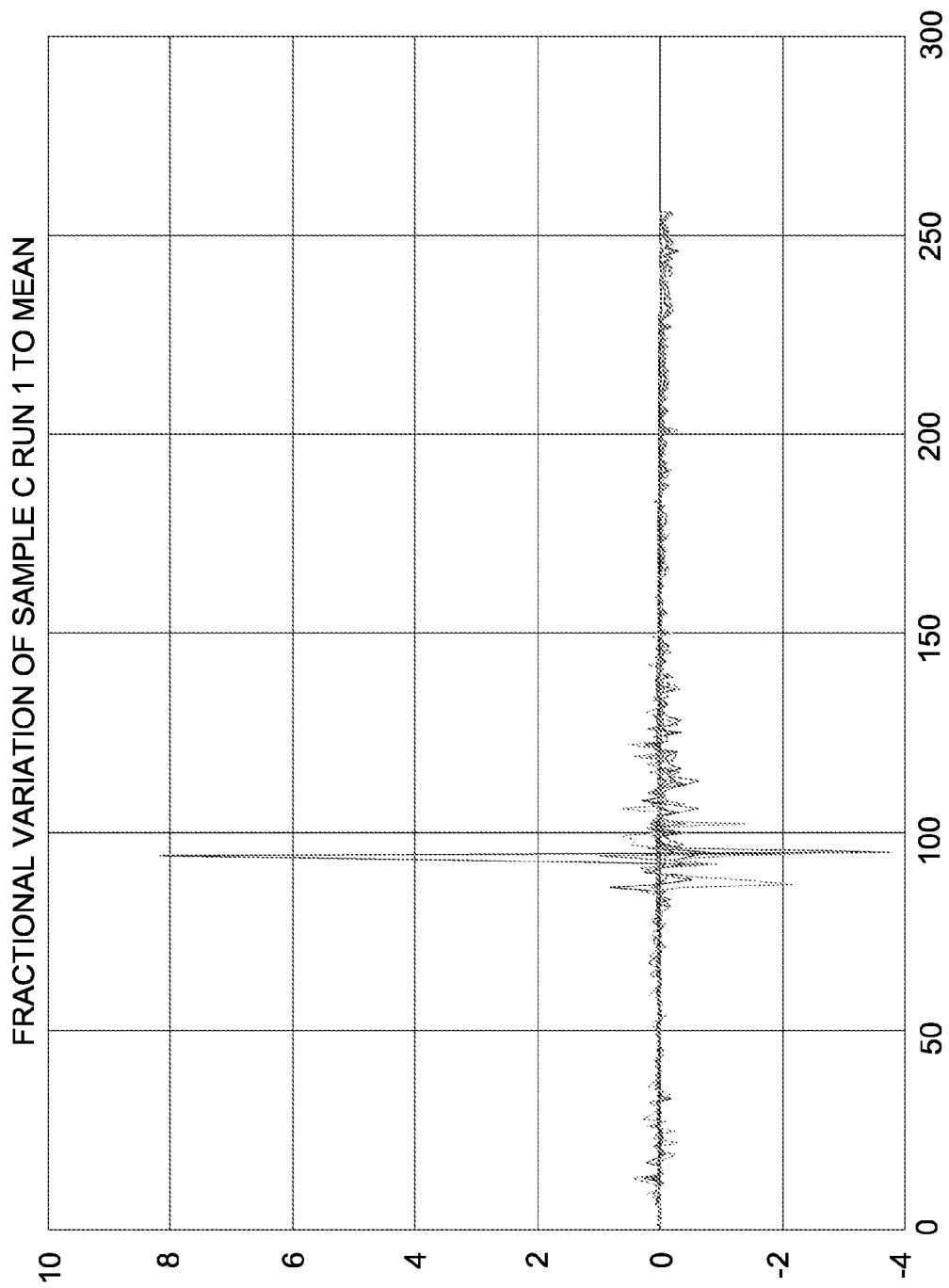
FIG. 9 is a plot of fractional differences of sample C movie and the mean movie.

FIG. 9 is a plot of fractional differences of one movie (of three) and a mean movie. Referring in particular to sample C, most of the variation occurs in the region of the window excised, i.e. pixels 90 –130. The dynamic range is –4 to +8.

Figure 10:
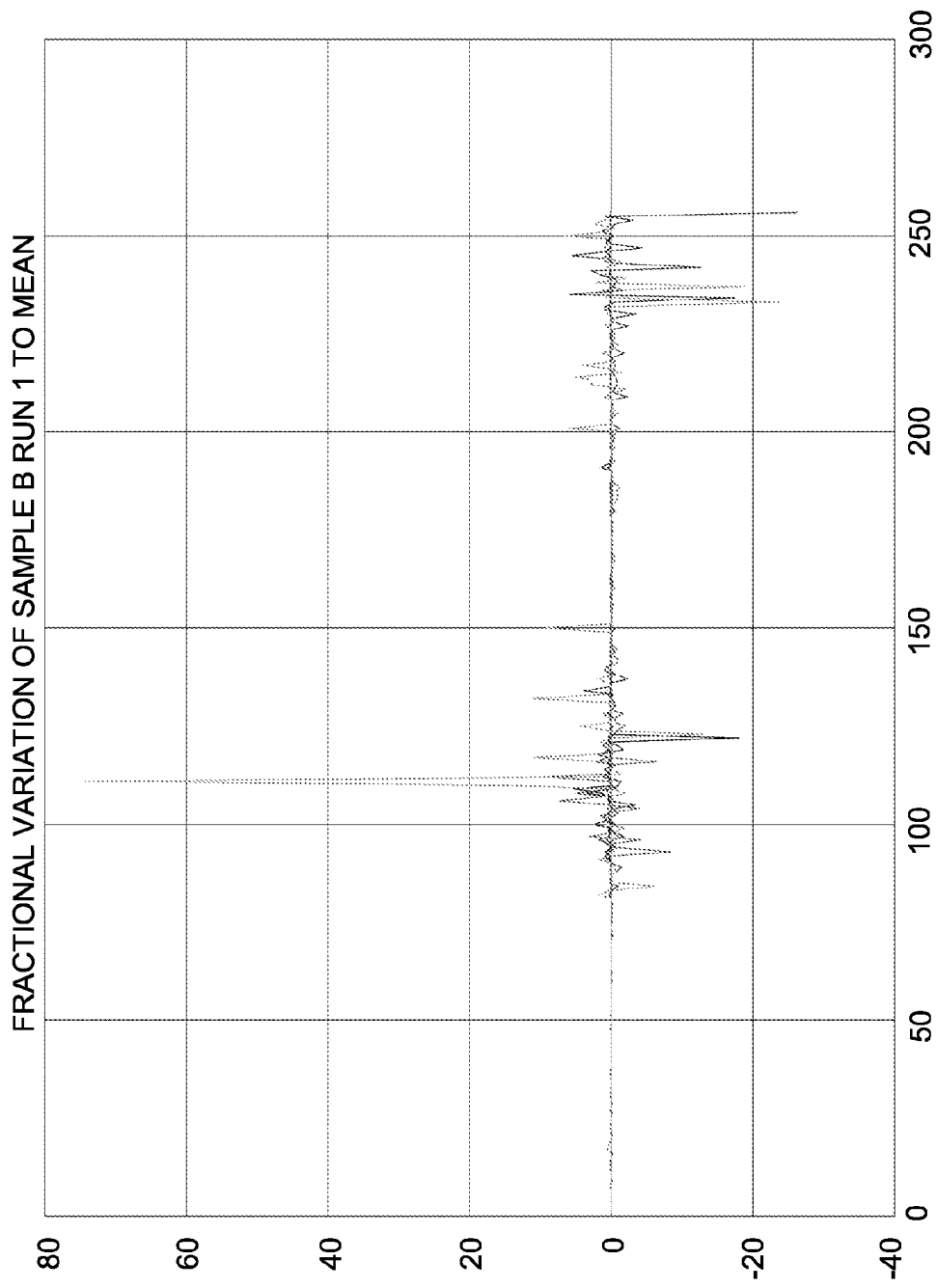
FIG. 10 is a plot of fractional differences for sample B as in FIG. 9.

In FIG. 10, one of the sample-B movies is generated under comparable conditions to those of FIG. 9. Not only is the amplitude of the variation in the 90-130 region dramatically higher for B, but there is also a huge variation in the 225+ region. No other samples have this problem.

It is possible that random instrument drift may account for some of the difference, However, variation in the second region was not accounted for, though it could have been. In other words, by adding more windows, problems of variability may be diminished.

A reasonable general rule that would be helpful in ensuring that measured variations are the result of real spectral differences rather than fluctuations near zero is all regions that have data within an $\epsilon$ of zero should be windowed out to the data points that are n$\epsilon$. Naturally, $\epsilon$ and n are particular to each system and are largely dependent on the noise. For example, a selection may be made to window out regions of the spectrum, which are less than 10 times the value of the noise. Clearly, this could be a larger burden for the higher frames of the movie since, in general, their signal is lower than that of the early frames.

Fractional differences are simply the difference of the individual run and the mean of the three runs divided by the mean of the three runs.

Once the quality of individual samples is determined then variations between samples can be reliably quantified. The mean value of each of the samples is compared in Table 3.

TABLE 3

|   | 6 | 7 | 8 | 9 | 10 | 11 |
|---|---|---|---|---|---|---|
| A to B | 1.8430 | 2.8524 | 5.2464 | 9.5216 | 19.5637 | 54.5614 |
| A to C | 1.8642 | 2.3544 | 2.8646 | 3.7874 | 4.3643 | 4.8240 |
| A to D | 1.2658 | 1.7450 | 2.2985 | 3.8122 | 4.5601 | 4.7147 |
| A to E | 5.5110 | 8.0512 | 10.2515 | 11.2953 | 12.5645 | 13.6896 |
| B to C | 0.6674 | 1.1397 | 3.3636 | 7.7673 | 33.8393 | 66.4533 |
| B to D | 1.7980 | 1.8870 | 3.6698 | 7.9811 | 26.8299 | 193.8976 |
| B to E | 6.9747 | 10.1578 | 13.7240 | 17.0529 | 21.8182 | 27.6169 |
| C to D | 2.0484 | 1.8036 | 1.8687 | 2.4527 | 3.0835 | 4.6691 |
| C to E | 7.1682 | 9.9882 | 12.3888 | 13.8554 | 15.1916 | 15.8287 |
| D to E | 5.6766 | 9.0567 | 11.7461 | 13.7298 | 15.3005 | 16.3190 |

In accordance with the invention, one way to carry out reproducibility measurements during on-line operation is to allow the sample to flow. In this way, every movie is taking measurements on fresh sample, not measured previously. This is the equivalent of moving the sample cup to examine different parts of the sample as done in the laboratory. Thus, a plurality of measurements, i.e. of movies, can be made during operation to ascertain the degree of reproducibility of in-line measurements. Naturally, this process is limited to those samples which themselves do not change appreciably during the measurement time of replicate movies. For example, if a movie takes 90 seconds to complete, three movies could take about 5 minutes. For a process that is completed in 15 minutes, this duration is much too long. The sample would undoubtedly be altered during this time. In such a situation, single movies done either on the flowing sample, or preferentially on a static sample, would be a favored approach. On the other hand, for a multi-hour process, five minutes of sample observation is likely to be the equivalent of a single point in time, with a virtually constant composition.

Mixture Homogeneity Detection

When a diffuse reflectance spectrum is measured with sufficient S/N to constitute a repeatable signal to within a specified tolerance, deviations from repeatability are indicators of a changing sample. The meaning of repeatable signal could be defined in at least two ways. The simpler method would be to look at the overall intensity of the signal by integrating the area under the spectral curve. This is equivalent to having a single detector that does not break the scattered light into a spectrum, but looks at the intensity of the overall beam. A more sophisticated way would be to calculate the RMS difference of subsequent spectra to quantify the variation. This is a particularly useful method when the inhomogeneity derives from poorly dispersed constituents, generating spectral differences because of compositional variations.

For an unchanging sample, there will be some variation of the diffuse reflectance spectrum attributable to random noise, instrument drift and other either controllable or uncontrollable variables. It is vital to know the repeatability limits of the instrument.

When measurements are made showing non-repeatable results, i.e. spectra outside the expected limits of error of the instrument, these results are indicative of a change in the sample. Since most on-line measurements of mixing/milling processes are done on flowing systems, the spectral result is really due to an average over a volume of material. For example, a near-IR fiber optic probe could be on a portal in a vat looking into a stirred stream; directly immersed into the stirred stream; or, at a sample cell that is part of a slip stream whereby some of the dispersion from the vat is pumped out and through the cell and generally allowed to return to the vat.

During the measurement interval a volume proportional to the measurement time passes through the detection region. As the detection time is increased, more fluid flows by and greater amounts of the dispersion are averaged. Conversely, shortening the measurement time is equivalent to looking at smaller volumes of the dispersion.

Now it is typically true that the larger the volume examined, the greater the degree of apparent homogeneity. Items present in low abundance, particularly large aggregates will appear to fluctuate greatly in number when small volumes are chosen. This result is a simple consequence of the standard deviation being proportional to the square root of the number of elements, N, and the relative deviation is just the inverse of this quantity or $N^{-1/2}$. As N gets larger, the relative error decreases.

A common way to manually assess the homogeneity of a dispersion is to remove a sample and place it between to microscope slides. Then it can be held to a light and examined for uniformity.

An improved, automated way to achieve the same goal, is to examine the near-IR (or indeed any other radiation that can be scattered from the dispersion) as a function of integration time of the measurement. For example, if a measurement is done over a 15 second interval, sampling the volume that traverses the probe in that time, the same type of measurement may be done over briefer intervals, say 10 seconds, 5 seconds, 1 second. The only criterion is that the repeatability of the system at these different integration times must be kept in mind. These criteria had previously been established with unchanging samples.

Thus, the homogeneity of the system can be derived from the time scale of integration, which is equivalently proportional to the volume of material, needed to obtain consistent results within the criteria of reproducibility.

The mixing/milling process frequently has multiple requirements including full dispersion of the chemicals and a grinding down of particle size. The time scales for each of the activities must be kept in mind. For example, the system may have rapidly become homogeneous but is undergoing constant and significant particle size reduction. This event, however, would be detectable by the consistent (monotonic) change in the series of spectra. An inhomogeneous system would have, on average, as many upward and downward fluctuations in the spectral data.

The quality of homogeneity of a dispersion undergoing a particular manufacturing process can be quantified by looking at the time scale needed to achieve repeatability of the signal. When doing so, it is important to make sure that flow rates are taken into consideration since a faster slipstream for example, would mean a greater amount of material per unit time and would give the illusion of greater homogeneity. It is good practice to fix the flow conditions to a specified reference standard before making conclusions about uniformity of the dispersion.

For a manufacturing process done according to a fixed protocol, the integration time procedure is a useful method of judging how close a product's uniformity is to that of previous successful products.

Validation of Components

A second measurement port may alternatively be used in the mixer either instead of or in addition the probe that observes the mixture. This would be a dual purpose cell capable of measuring either in transmission or reflectance to examine incoming material and compare its spectrum to a database of known materials. In one embodiment, the sample cell would be multiplexed to make either type of measurement. In the other, only a transmission or a reflectance measurement would be needed.

For example, in the manufacture of dispersions comprised entirely of transparent liquid materials, only a transmission cell would be needed. In the case of a more complex mixture involving powders, a dual cell would be appropriate, or just a diffuse reflectance cell for the case that only the powders are of concern.

The cell may have a single light source and a fiber or other optical method to couple diffuse reflectance from the front surface. It would also be equipped with a fiber at the rear of the cell opposite the illumination, for transmission measurements. In another embodiment, no fiber optics would be necessary; a detector would be inline.

Another way to implement this cell would be in series, where the first cell is in transmission mode and the second is in reflectance, or vice versa.

As material is added, the spectra are taken. For a given flow rate measured with an auxiliary device, the amount of material inserted can be determined by the duration of time that the spectrum of the particular material is measured. Alternatively, a weighing device may be used.

A computer or similar storage device records this information for later retrieval to validate the addition of proper components.

In a preferred embodiment, the full mixture is monitored with the near-IR, as well, to verify that that the particle size and overall composition of the mixture is as required.

Laser Method to Examine Creams

Figure 11:
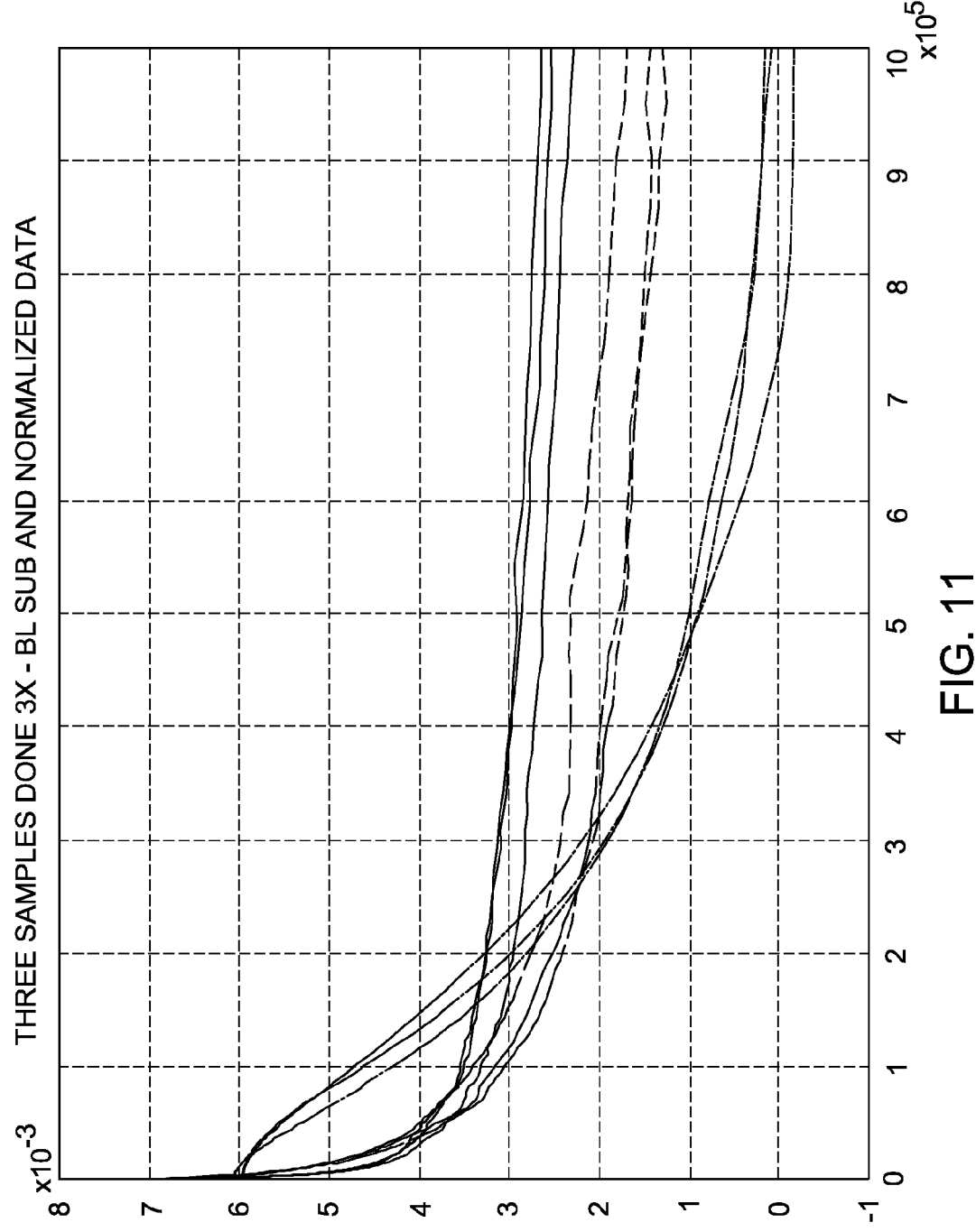
FIG. 11 is a plot of correlation functions for three creams.

FIG. 11 shows autocorrelation data from laser light scattering in three cream samples. Notwithstanding that the classical diffusion theory is suspended for interpretation of the data, the fact that reproducible correlation functions are obtainable is significant.

The objective is to be able to associate particular correlation functions with specific chemical compositions. In this way, the correlation-data strategy resembles much of the earlier discussion of broadband analyses. Both methods rely on the prior knowledge of a defined goal material, and both accumulate standard results which can be stored and used later for comparison with new samples. This association of a particular shape correlation function with a specific product or with a product in a stage of being processed is useful for making distinctions among products with similar appearance. More importantly, it can be used as a set of curves representing a cream or lotion during manufacturing. The correlation measurements can be made on the samples, preferably online, during mixing/milling to determine the current state of the system. By comparing the correlation functions to a known set taken as a library reference, the operator can judge the current condition of the process. The process can then be terminated when the curve corresponding to the finished sample is obtained.

The raw correlation function is subject to variations that significantly modify its appearance, but in ways unrelated to the chemical system. These artifacts need to be eliminated. First, subtract the theoretical baseline from all of the samples. Correlation functions have baselines equal to the product of the total number of counts times the square of the average number of counts per channel. Then consider the possible statistical variation in the laser coherence, a phenomenon that is likely to vary significantly in very short time intervals, maybe even as short as a second. This fluctuation impacts the overall amplitude after baseline subtraction. When this fluctuation is taken into consideration simply by normalizing the remaining correlation function, the results shown in FIG. 11 are obtained. This figure shows data taken in triplicate for cream samples in three states of manufacture.

There are numerous ways to characterize the evolving correlation functions. One way is to use the standard cumulant analysis, which after the filtering already done is basically a polynomial description of the curve. This can be done to arbitrary order, though in practice it is rarely carried out beyond fourth order.

A second way would be to assemble a series of samples and measure their correlation functions and then perform a cluster analysis so that particular formulations would be associated with a given cluster. A measured unknown could be assessed for membership in or proximity to a given cluster.

It should be understood that the foregoing description is only illustrative of the invention. Various alternatives and modifications can be devised by those skilled in the art without departing from the invention. Accordingly, the present invention is intended to embrace all such alternatives, modifications and variances, which fall within the scope of the appended claims.

What is claimed is:

1. A method for determining characteristics of a material comprising:
   illuminating the material with coherent light so as to produce scattered light;
   producing a signal representative of the scattered light;
   autocorrelating said signal representative of the scattered light;
   preprocessing a signal representative of the scattered light to produce a processed signal;
   comparing the processed signal with standard library reference correlation functions for the material to determine whether the material is in a particular product stage;
   varying distance between a first light conductor for conducting light to said material and a second light conductor for conducting light from said material so as to vary distance that light travels through the material;
   evaluating light received from said material at a plurality of distances between said first light conductor and said second light conductor; and
   analyzing a plurality of spectra produced at a plurality of distances of said first light conductor from said second light conductor to generate a three dimensional surface for said comparing.

2. The method of claim 1, further comprising performing at least one of a cumulant analysis and a cluster analysis of said processed signal to provide analyzed data to associate with said particular characteristics of said material.

3. The method of claim 1, wherein preprocessing comprises one or more baseline estimations.

4. The method of claim 3, wherein said one or more baseline estimations comprises subtracting of a product of a total number of sums and the square of the average number of counts per channel.

5. The method of claim 1, wherein preprocessing comprises normalization of a post-baseline-corrected autocorrelation function.

6. The method of claim 1, further comprising establishing criteria of repeatability.

7. The method of claim 1, wherein the material comprises an optically highly scattering fluid.

8. The method of claim 1, wherein the material comprises an emulsion.

9. The method of claim 1, where the material comprises cream or lotion for pharmaceutical or cosmetic purposes.

10. The method of claim 1, wherein the material comprises one of an ink or paint.

11. The method of claim 1, wherein the material comprises a fluidized composite mixture.

12. A method for monitoring a process for altering a state of a material to determine characteristics of the material, comprising:
    illuminating the material with coherent light so as to produce scattered light;
    producing a signal representative of the scattered light;
    autocorrelating said signal representative of the scattered light;
    preprocessing a signal representative of the scattered light to produce a processed signal;
    comparing the processed signal with standard library reference correlation functions for the material to determine whether the material undergoing the process is in a particular product stage of being processed;
    varying distance between a first light conductor for conducting light to said material and a second light conductor for conducting light from said material so as to vary distance that light travels through the material;
    evaluating light received from said material at a plurality of distances between said first light conductor and said second light conductor; and
    analyzing a plurality of spectra produced at a plurality of distances of said first light conductor from said second light conductor to generate a three dimensional surface for said comparing.

13. The method of claim 12, further comprising performing at least one of a cumulant analysis and a cluster analysis of said processed signal to provide analyzed data to associate with said particular characteristics of said material.

14. The method of claim 12, wherein the monitoring is performed in real time as the material is altered.

15. The method of claim 13, further comprising using a determination of the characteristics of the material to accomplish at least one or more of altering or terminating the process.

16. The method of claim 12, wherein preprocessing comprises one or more baseline estimations.

17. The method of claim 16, wherein said one or more baseline estimations comprises subtracting of a product of a total number of sums and the square of the average number of counts per channel.

18. The method of claim 12, wherein preprocessing comprises normalization of a post-baseline-corrected autocorrelation function.

19. The method of claim 12, further comprising establishing criteria of repeatability.

20. An apparatus for determining characteristics of a material comprising:
    a laser for illuminating the material with coherent light so as to produce scattered light;
    a detector for producing a signal representative of the scattered light;
    a processor for autocorrelating said signal representative of the scattered light;
    a processor for preprocessing a signal representative of the scattered light to produce a processed signal;
    a processor for comparing the processed signals with standard library reference correlation functions for the material to determine whether the material is in a particular
    means for moving, at a plurality of different times, one or more of a first light conductor for conducting light to said material and a second light conductor for conducting light from said material to vary distance between the first light conductor and the second light conductor so as to vary distance that light travels through the material; and means for analyzing a plurality of spectra produced at a plurality of distances of said first light conductor from said second light conductor to generate a three dimensional surface for said comparing product stage.

21. The apparatus of claim 20, further comprising an additional processor for performing at least one of a cumulant analysis and a cluster analysis of said processed signal to provide analyzed data to associate with said particular characteristics of said material.

22. The apparatus of claim 20, further comprising means for establishing criteria of repeatability of analyzed data.

* * * * *